United States Patent
Ikemoto

(10) Patent No.: US 10,100,055 B2
(45) Date of Patent: Oct. 16, 2018

(54) IMIDAZOPYRROLOQUINOLINE SALT, METHOD FOR PRODUCING THE SAME, MEDICAMENT, COSMETIC, AND FOOD

(71) Applicant: Mitsubishi Gas Chemical Company, Inc., Chiyoda-ku (JP)

(72) Inventor: Kazuto Ikemoto, Niigata (JP)

(73) Assignee: MITSUIBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 15/845,112

(22) Filed: Dec. 18, 2017

(65) Prior Publication Data

US 2018/0186794 A1 Jul. 5, 2018

(30) Foreign Application Priority Data

Dec. 26, 2016 (JP) ................... 2016-250850

(51) Int. Cl.

| | | |
|---|---|---|
| *C07D 471/18* | (2006.01) | |
| *A61K 31/4748* | (2006.01) | |
| *C07D 471/16* | (2006.01) | |
| *A23L 33/10* | (2016.01) | |
| *A61K 8/49* | (2006.01) | |

(52) U.S. Cl.
CPC ............ *C07D 471/16* (2013.01); *A23L 33/10* (2016.08); *A61K 8/4946* (2013.01); *A23V 2002/00* (2013.01)

(58) Field of Classification Search
CPC ............. C07D 471/18; A61K 31/4748; A23V 2002/00
USPC ..................... 546/64; 514/287; 424/401, 439
See application file for complete search history.

(56) References Cited

FOREIGN PATENT DOCUMENTS

| | | |
|---|---|---|
| JP | 09-040675 | 2/1997 |
| JP | 2015-189711 | 11/2015 |

OTHER PUBLICATIONS

A. E. Mitchell, et al., Analytical Biochemistry 269, 1999, pp. 317-325.
Toshimasa Ishida, et al., "Formation of Imidazolopyrroloquinoline as Main PQQ Adduct with Amino Acid in Vitro: X-Ray Structural Evidence," J. Am. Chem. Soc., 1995, pp. 3278-3279.

*Primary Examiner* — Charanjit Aulakh
(74) *Attorney, Agent, or Firm* — Oblon, McClelland, Maier & Neustadt, L.L.P.

(57) ABSTRACT

There is provided a production method for the purpose of improving the solubility of an arginine-residue imidazopyrroloquinoline in water and making the purity thereof high. There is provided a compound represented by general formula (1):

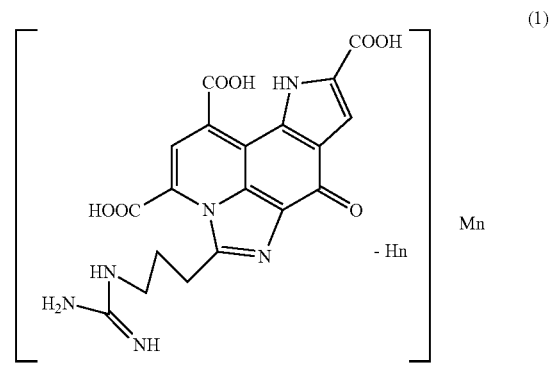

wherein n is 1, 2, 3 or 4; and M is an alkali metal or ammonium.

9 Claims, 1 Drawing Sheet

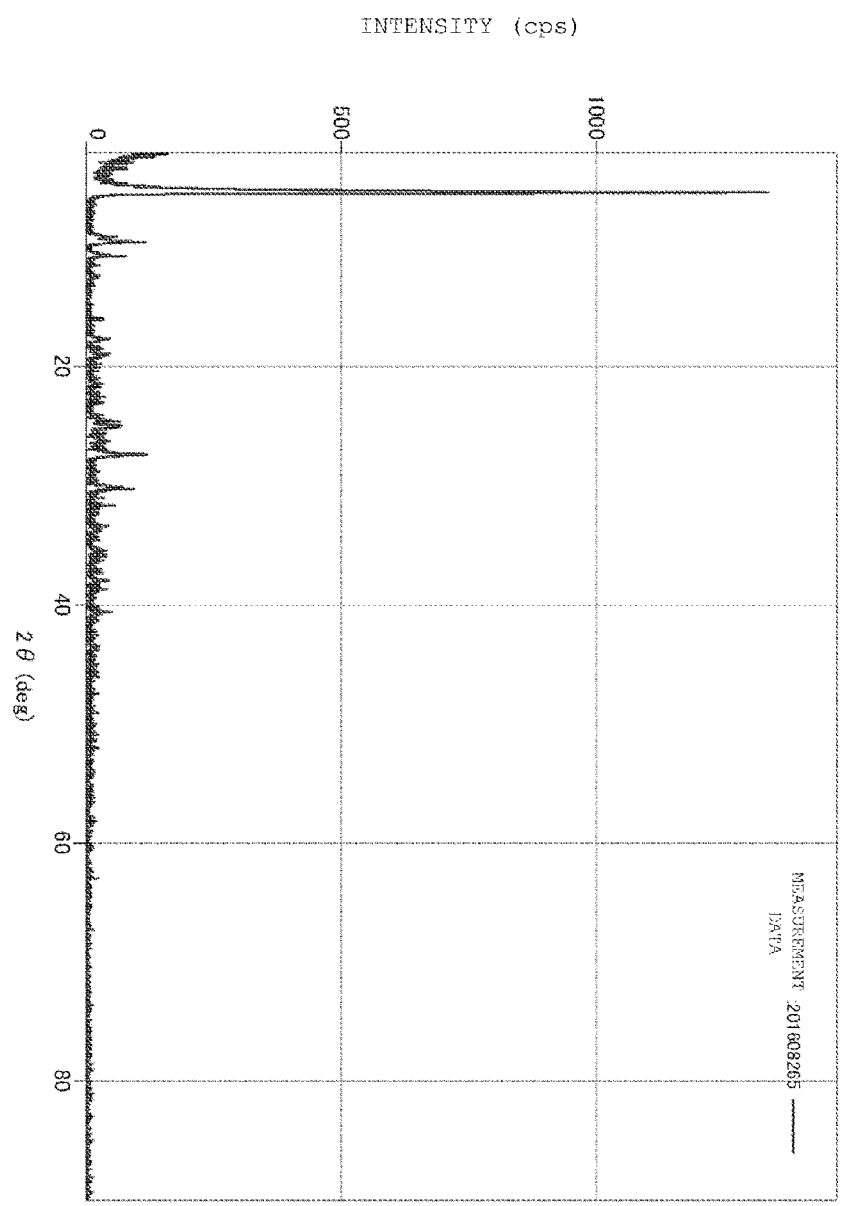

IMIDAZOPYRROLOQUINOLINE SALT, METHOD FOR PRODUCING THE SAME, MEDICAMENT, COSMETIC, AND FOOD

BACKGROUND ON THE INVENTION

Field of the Invention

The present invention relates to an imidazopyrroloquinoline salt and a method for producing the same, and a medicine, a cosmetic and a food.

Description of the Related Art

Imidazopyrroloquinoline (hereinafter, referred to also as "IPQ"), particularly an imidazopyrroloquinoline having an arginine residue (hereinafter, referred to also as "arginine-residue imidazopyrroloquinoline" or "argIPQ"), is a substance having a physiological activity, and an important substance to be used for medicines or functional foods. Then, it is known that IPQ such as argIPQ is contained in foods (for example, see Analytical Biochemistry 269, 317-325 (1999)), and the IPQ is a molecule having functionality also in foods.

As a method for synthesizing an IPQ such as an argIPQ, there is disclosed a method for obtaining the IPQ by reacting pyrroloquinoline quinone with an amino acid (for example, see J. Am. Chem. Soc., 1995, 117, p 3278-3279, Japanese Patent Laid-Open No. 09-040675).

Further as an analogous substance of IPQ, an alkali metal salt of imidazopyrroloquinoline having no arginine residue is disclosed so far (for example, see Japanese Patent Laid-Open No. 2015-189711).

An argIPQ obtained by conventional synthesis methods, however, is a mixture, not a single component. Further, these methods are difficult to be practically utilized as industrial production method. For example, in J. Am. Chem. Soc., 1995, 117, p 3278-3279, the presence of IPQ is confirmed as a peak in a liquid chromatograph. However, argIPQ is obtained not in a high purity state, and it is difficult to produce an argIPQ as a single substance, and it is also difficult to examine the physiological activity of the argIPQ.

Further the argIPQ can be extracted by liquid chromatography; however, in order to industrially produce the argIPQ, a solvent to be used for a mobile phase for its separation is needed in a large amount. Further since the concentration of the argIPQ to be handled is low, it is difficult to crystallize the argIPQ.

Then, for an alkali metal salt of imidazopyrroloquinoline disclosed in Japanese Patent Laid-Open No. 2015-189711, the physical properties of the alkali metal salt can be predicted mainly by using the number of carboxylic acids the alkali metal salt has. For an imidazopyrroloquinoline further having an arginine residue, however, it is not easy to predict the physical properties of its salt. Additionally, it is considered that for the alkali metal salt of imidazopyrroloquinoline obtained by a conventional synthesis method, the more excessively its raw materials are present, the more easily the reaction progresses.

Here, for the argIPQ, in order to improve the handleability in preparation as, for example, medicines, the solubility in water is required to be excellent. Further, the argIPQ is required also to be a substance stable as a crystal.

It is further required as described above that the argIPQ can be obtained as a single substance and can be obtained by a simple production method with high productivity.

Then, an object of the present invention is to provide a novel compound excellent in the solubility in water and having a structure of an arginine-residue imidazopyrroloquinoline (argIPQ).

SUMMARY OF THE INVENTION

As a result of exhaustive studies to produce a substance having an excellent solubility in water and stable when made into a crystal, the present inventor has found that a compound in a form of a predetermined salt having a structure of an argIPQ is excellent in the solubility and the thermal stability, and this finding has led to the present invention.

That is, the present invention is as follows.

[1]
A compound, being represented by general formula (1):

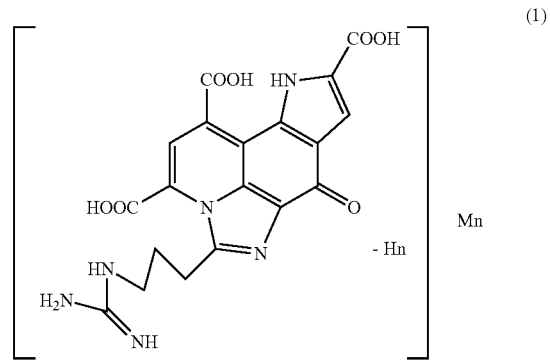

wherein n is 1, 2, 3 or 4; and M is an alkali metal or ammonium.

[2]
The compound according to [1],
wherein the M is an alkali metal, and
the alkali metal is any of Na, K and Li.

[3]
The compound according to [2],
wherein the compound is a disodium salt.

[4]
The compound according to [3],
wherein the compound is a hydrous crystal.

[5]
A method for producing a compound, comprising
a recovery step of recovering a substance depositing by a reaction of a pyrroloquinoline quinone sodium salt with arginine to thereby obtain a compound according to [3] or [4].

[6]
The method for producing the compound according to [5],
wherein in the recovery step, the amount of the arginine to be used is 0.3 or more times and 5.0 or less times the mass of the pyrroloquinoline quinone sodium salt.

[7]
A medicine, comprising
the compound according to any one of [1] to [4].

[8]
A cosmetic, comprising
the compound according to any one of [1] to [4].

[9]
A food, comprising
the compound according to any one of [1] to [4].

Advantageous Effects of the Invention

The compound according to the present invention enables the use of the compound excellent in the solubility in water and having a structure of an argIPQ. Further, the method for producing the compound according to the present invention makes it possible to produce the compound easily and simply, and inexpensively and in a large amount. Further, the compound, when used for medicines, cosmetics or foods, enables easy preparation.

BRIEF DESCRIPTION OF THE DRAWING

The FIGURE shows a measurement result of powder X-ray diffractometry of an arginine-substituted IPQ disodium trihydrate.

DETAILED DESCRIPTION OF THE PREFERRED EMBODIMENT

Hereinafter, the preferred embodiment of the present invention (hereinafter, referred to as "the present embodiment") will be described in detail. The following present embodiment is an exemplification to illustrate the present invention, and is not intended to limit the present invention to the following content. Suitable changes and modifications may be made within the gist of the present invention to carry out the present invention.

<argIPQ Salt>

A compound (hereinafter, referred to also as "arginine-residue imidazopyrroloquinoline salt" or "argIPQ salt") of the present embodiment is a compound represented by the general formula (1). Here, the "argIPQ salt" is a salt of 5-(3-guanidinopropyl)-7-oxo-7,10-dihydroimidazo[4,5,1-ij]pyrrolo[2,3-f]quinoline-1,3,9-tricarboxylic acid.

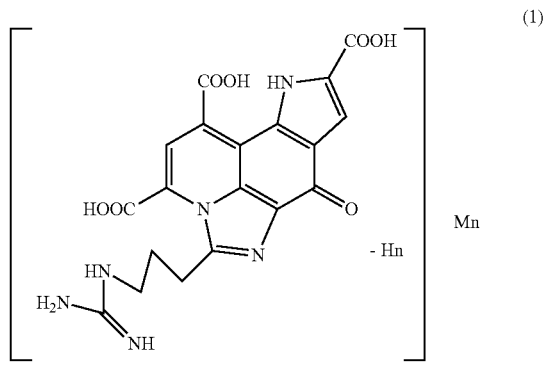

(1)

wherein n is 1, 2, 3 or 4; and M is an alkali metal or ammonium.

The compound of the present embodiment enables the use of the compound excellent in the solubility in water and having a structure of an argIPQ. The cause is conceivably as follows (however, the cause is not limited thereto). A conventional compound having a structure of an argIPQ has both a guanidine group, which is basic, and carboxylic acids, which are acidic, and is, due to being hence liable to form an intramolecular salt, unlikely to hydrate and is poor in the solubility in water. The compound of the present embodiment, however, due to that an alkali metal or ammonium is an ion bonded to the carboxylic acid, easily causes hydration on the cation side of the alkali metal or the ammonium and is excellent in the solubility in water.

The compound of the present embodiment is a salt of an argIPQ with an alkali metal or ammonium. The number (n) of the alkali metals added to the argIPQ is any of 1, 2, 3 or 4, preferably any of 2, 3 or 4, and more preferably 2. The alkali metal is preferably any of sodium (Na), potassium (K) and lithium (Li), more preferably any of sodium (Na) and potassium (K), and still more preferably sodium (Na). When the alkali metal is any of sodium (Na), potassium (K) and lithium (Li), the solubility of the argIPQ salt in water tends to be improved. Further it is likely that when the alkali metal is any of sodium (Na) and potassium (K), the compound of the present embodiment is less likely to exhibit an adverse action on humans and when the compound of the present embodiment is used as an alkaline solution, amine odor is less likely to be generated.

In the molecular structure of the argIPQ, as sites where a hydrogen ion is easily released, there are four sites of three sites on three carboxylic acids and one site on an imidazole group, but the argIPQ is allowed to release a hydrogen ion on either of any one of the carboxylic acids and the imidazole group to form a salt. It is generally difficult to specify the releasing site and the releasing site may change depending on the crystal state of the argIPQ salt. Further, the argIPQ salt of the present embodiment is allowed to coexist with an alkali metal compound.

The argIPQ salt of the present embodiment may be a hydrous salt. The hydrous salt is also called a hydrate. Examples of the hydrous salt include a monohydrate, a dihydrate, a trihydrate and a tetrahydrate of the argIPQ.

Since the argIPQ salt of the present embodiment can form a more stable crystal, it is more preferable that the argIPQ salt be a disodium salt of the argIPQ, which has a high crystallinity. Examples of the disodium salt of the argIPQ include a compound represented by the following formula.

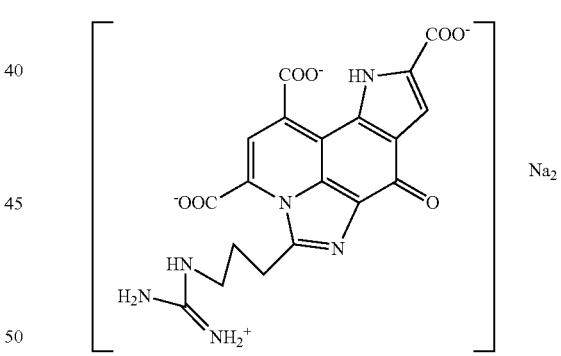

Since the argIPQ salt has a guanidine structure in the arginine substituent moiety, ions may be formed at the substituent moiety. In the case where the argIPQ salt is a disodium salt, the disodium salt, when depositing, easily crystallizes. Then, the deposit of the disodium salt, since it deposits in excellent crystallinity, has a high purity and an excellent solubility in water. Further the disodium salt is more preferably a hydrous crystal, and from the viewpoint of the crystallinity, still more preferably a hydrous crystal of a trihydrate and/or a monohydrate. When the disodium salt is a hydrous crystal, the solubility of the argIPQ salt in water is likely to be more improved. Further when the disodium salt is a hydrous crystal, it is likely that the argIPQ salt becomes unlikely to susceptible to the weight change by moisture absorption and is industrially easily utilized.

<Method for Producing the argIPQ Salt>

A method for producing the argIPQ salt of the present embodiment comprises a step of reacting an alkali metal salt of pyrroloquinoline quinone or an ammonium salt of pyrroloquinoline quinone with arginine. The step can use an organic solvent such as ethanol, water or both thereof, but preferably involves the reaction in an aqueous solution using water. Then, the reaction is carried out preferably in a heated state, more preferably at 20° C. to 180° C., and still more preferably at 50° C. to 130° C. When the reaction is carried out in such a temperature range, since an obtained reaction product is likely to be produced in a suitable time, the step is industrially preferable. Further when the reaction is carried out in such a temperature range, no pressure vessel nor the like becomes necessary in the step.

According to the method for producing the argIPQ salt of the present embodiment, a conventional refinement step can be simplified. Since there deposits the argIPQ salt obtained by the reaction of an alkali metal salt of pyrroloquinoline quinone or an ammonium salt of pyrroloquinoline quinone with arginine, the method for producing the argIPQ salt of the present embodiment can easily separate the deposit from unreacted alkali metal salt of pyrroloquinoline quinone or ammonium salt of pyrroloquinoline quinone and arginine.

The concentration of the alkali metal salt of pyrroloquinoline quinone or the ammonium salt of pyrroloquinoline quinone when used in the reaction, particularly when industrially reacted, is, with respect to the total amount (100% by mass) of the alkali metal salt of pyrroloquinoline quinone or the ammonium salt of pyrroloquinoline quinone and arginine, preferably 0.05% by mass or more and 85% by mass or less, more preferably 0.1% by mass or more and 50% by mass or less, and still more preferably 30% by mass or more and 70% by mass or less. When the concentration is in the above range, it is likely that the argIPQ salt can be directly obtained.

The amount of arginine to be used is preferably 0.3 or more times and 5.0 or less times the mass of the alkali metal salt of pyrroloquinoline quinone or the ammonium salt of pyrroloquinoline quinone. When the amount of arginine to be used is in such a range, the reactivity is likely to be more improved.

The pH in the reaction is not especially limited, but being 2 to 7 is likely to make the reaction to progress easily.

The reaction can be carried out in a solution state or in a suspension state.

The progress of the reaction can be observed by using common analysis means such as liquid chromatography or paper chromatography. Further in the production method of the present embodiment, the argIPQ salt being the target deposits from reaction products, and can further be refined by a well-known method. The refining method can be one using recrystallization or one of various types of chromatography. According to the method, the purity of the argIPQ salt can be raised.

When the reaction temperature is regulated at 0 to 100° C., the argIPQ salt is likely to easily deposit as a crystal. Generally, when one of the alkali metal salt of pyrroloquinoline quinone or the ammonium salt of pyrroloquinoline quinone and arginine is used excessively in the reaction, a suitable range of making the reaction to progress more easily is applied to the present invention.

Forms as raw materials of the alkali metal salt of pyrroloquinoline quinone or the ammonium salt of pyrroloquinoline quinone may be in any form, and for example, the alkali metal salt of pyrroloquinoline quinone may be formed by neutralizing a free form of pyrroloquinoline quinone and an alkali metal compound in a reaction system. Further in the case where the pyrroloquinoline quinone is a form of a free form of pyrroloquinoline quinone, by making an alkali metal salt, for example, sodium chloride, for the pyrroloquinoline quinone to coexist in the reaction, the alkali metal salt of pyrroloquinoline quinone can also be formed. Here, the "free form" means pyrroloquinoline quinone forming no salt.

The alkali metal salt of pyrroloquinoline quinone or the ammonium salt of pyrroloquinoline quinone is preferably a salt of pyrroloquinoline quinone with any of sodium, potassium, lithium and ammonium. The cation moiety when the salt is formed is determined by a cation coexisting in the deposition. The alkali metal salt of pyrroloquinoline quinone or the ammonium salt of pyrroloquinoline quinone is more preferably a sodium salt, and still more preferably a disodium salt.

In the method for producing the argIPQ salt of the present embodiment, it is preferable, because the argIPQ salt can be refined more easily, that the step of reacting an alkali metal salt of pyrroloquinoline quinone or an ammonium salt of pyrroloquinoline quinone with arginine be a recovery step of recovering a substance depositing by the reaction of pyrroloquinoline quinone disodium with arginine to thereby obtain an argIPQ disodium salt. By incorporating such a recovery step, an argIPQ disodium salt depositing by the reaction in water can be separated more easily from unreacted pyrroloquinoline quinone disodium and arginine.

The production method will be described more specifically. Pyrroloquinoline quinone disodium and arginine are mixed in water. At this time, the mixing can be carried out at 0° C. to 120° C., but 20° C. to 100° C. is preferable. The reaction time is preferably 1 hour to 5 days. In the production method of the present embodiment, since an argIPQ salt deposits as a crystal, by separating the crystal by filtration or centrifugation, a high-purity argIPQ salt can be obtained. The obtained crystal is washed and dried by common methods. The argIPQ disodium is a hydrous crystal, and is likely to be obtained as a trihydrate. By further drying the trihydrate, a monohydrate crystal thereof can also be obtained.

The argIPQ salt of the present embodiment can be provided in a form of a hard capsule, a soft capsule or a tablet. At this time, the argIPQ salt may be mixed with other additives and the like.

The argIPQ salt, by utilizing the high solubility thereof in water, can be used as medicines, cosmetics, foods and feed, and can also be used particularly as infusion solutions, injection solutions and beverages. It is also easy for the argIPQ salt, for example, to be mixed with an emulsifying material and blended in cosmetic creams and cakes. It is also easy for the argIPQ salt to be mixed in rice or wheat powder, and the argIPQ salt can also be used for foods by utilizing the mixture.

EXAMPLES

Hereinafter, the present embodiment will be described more specifically by way of Examples and Comparative Example, but the present embodiment is not any more limited to these Examples. In the Examples and the Comparative Example shown hereinafter, unless otherwise specified, reagents used were ones manufactured by Wako Pure Chemical Industries, Ltd. Further the ultraviolet absorption spectra were measured by using an "UV1800" by trade name, manufactured by Shimadzu Corp. The liquid chromatography (LC) was measured by using an "LC-2010" by trade name, manufactured by Shimadzu Corp., under the following conditions.

LC Conditions
Measurement wavelength: 259 nm
Measurement temperature: 40° C.
Column: YMC-Pack ODS-A 150 mm, 4.6 mm
Mobile phase: 30 mM acetic acid-70 mM ammonium acetate

[Example 1] Synthesis of an argIPQ (Raw Material: PQQ Disodium)

1 g of PQQ disodium (trade name: "BioPQQ," manufactured by Mitsubishi Gas Chemical Co., Inc.) and 1 g of arginine were mixed with 20 mL of water, stirred at room temperature for 30 min or more to thereby obtain a mixture. The mixture was heated to 70° C., and allowed to react for 1 day. After the reaction, it was confirmed that a yellow solid deposited in the liquid. Thereafter, the resultant was cooled to room temperature, and filtered to thereby obtain a yellow solid. The yellow solid was washed with 10 mL of ethanol, and vacuum dried at room temperature for 12 hours to thereby obtain 1.3 g of a yellow crystal.

The obtained crystal was subjected to liquid chromatography. A peak appeared at 23.7 min and the purity determined by the liquid chromatography was 99%.

It was confirmed from the result by elemental analysis that the obtained crystal was a hydrate and was an argIPQ disodium trihydrate. The result by elemental analysis and theoretical values of the argIPQ disodium trihydrate are shown below.

Elemental analysis: C: 38.73, H: 4.47, N: 14.56.
Calculated values: C: 38.73, H: 4.47, N: 14.56.

The molecular structure of the obtained crystal was identified by a nuclear magnetic resonance method as follows. Heavy methanol was added to the obtained crystal until saturated; thereafter, the resultant was centrifuged to remove a solid, for which the molecular structure was measured by a nuclear magnetic resonance instrument (trade name: "JNM-ECA500 Spectrometer," manufactured by JEOL Ltd.). The results are shown below. $^1$H-NMR (internal standard: trimethylsilane (TMS))

The results are shown in the order of chemical shift (ppm), (integral ratio) and cleavage pattern.

2.17 (2) t, 3.27 (4) m, 7.27 (1) s, 7.81 s (1)

From the above results and the above elemental analysis results, the molecular structure of the crystal was identified to be an argIPQ disodium.

A powder X-ray diffraction of the obtained crystal was measured by using an X-ray diffractometer (X'Pert Pro, manufactured by PANanalytical B.V., CuKα: λ=1.5405 Å, 45 kV-40 mA), and a characteristic peak was confirmed at the position of 2θ=5.371 (FIGURE). Further confirmed peaks are collectively shown in the following table.

TABLE 1

| No. | 2θ (deg) | d (Å) | Peak height (cps) |
|---|---|---|---|
| 1 | 5.371(8) | 16.44(2) | 701(48) |
| 2 | 9.46(2) | 9.34(2) | 49(13) |
| 3 | 10.701(14) | 8.260(11) | 19(8) |
| 4 | 17.64(5) | 5.022(14) | 19(8) |
| 5 | 19.118(19) | 4.639(5) | 14(7) |
| 6 | 24.89(10) | 3.574(14) | 21(8) |
| 7 | 27.33(2) | 3.260(2) | 63(14) |

TABLE 1-continued

| No. | 2θ (deg) | d (Å) | Peak height (cps) |
|---|---|---|---|
| 8 | 30.11(5) | 2.966(5) | 40(12) |
| 9 | 33.67(16) | 2.660(12) | 5(4) |

[Example 2] An argIPQ (Raw Material: PQQ Trisodium)

40 g of PQQ disodium (trade name: "BioPQQ," manufactured by Mitsubishi Gas Chemical Co., Inc.) was mixed with 0.4 L of water to thereby obtain a mixture. Thereafter, a 25% sodium hydroxide aqueous solution and hydrochloric acid were added in proper amounts to regulate the pH of the mixture at 7. Then, 83 g of sodium chloride and 500 mL of water were mixed under stirring in the mixture; and crystallization was carried out at 50° C. for 3 days. Thereafter, the resultant was cooled to room temperature, and filtered to thereby obtain a red solid. The red solid was washed with 10 mL of ethanol, and vacuum dried at room temperature for 12 hours to thereby obtain 42.9 q of PQQ trisodium.

1 g of the obtained PQQ trisodium, 1 g of arginine and 25 mL of water were mixed, and stirred for 30 min or more at room temperature to thereby obtain a mixture. The mixture was heated to 70° C., and allowed to react for 3 days. After the reaction, it was confirmed that a yellow solid deposited in the liquid. Thereafter, the resultant was cooled to room temperature, and filtered to thereby obtain a yellow solid. The yellow solid was washed with 10 mL of ethanol, and vacuum dried at room temperature for 12 hours to thereby obtain 0.76 g of a yellow crystal.

The obtained crystal was subjected to liquid chromatography and the elution time was the same as that in the liquid chromatography in Example 1. The purity was 99%.

It was confirmed from the result by elemental analysis that the obtained crystal was a hydrate and was an argIPQ disodium trihydrate. The result by elemental analysis and theoretical values of the argIPQ disodium trihydrate are shown below.

Elemental analysis: C: 38.58, H: 4.47, N: 14.17.
Calculated values: C: 38.73, H: 4.47, N: 14.56.

[Example 3] an argIPQ (Raw Material: PQQ Free Form)

A PQQ free form was obtained by a reaction of PQQ disodium (trade name: "BioPQQ," manufactured by Mitsubishi Gas Chemical Co., Inc.) with hydrochloric acid.

1 g of the obtained PQQ free form, 0.8 g of a 25% sodium hydroxide aqueous solution, 1 g of arginine and 25 mL of water were mixed, and stirred for 30 min or more at room temperature to thereby obtain a mixture. The mixture was heated to 70° C., and allowed to react for 3 days. After the reaction, it was confirmed that a yellow solid deposited in the liquid. Thereafter, the resultant was cooled to room temperature, and filtered to thereby obtain a solid. The solid was washed with 10 mL of ethanol, and vacuum dried at room temperature for 12 hours to thereby obtain 0.69 q of a yellow crystal.

It was confirmed from the result by elemental analysis that the obtained crystal was a hydrate and was an argIPQ disodium trihydrate. The result by elemental analysis and theoretical values of the argIPQ disodium trihydrate are shown below.

The obtained crystal was subjected to liquid chromatography and coincided with the result of the liquid chromatography in Example 1. The purity was 99%.

Elemental analysis: C: 38.50, H: 4.35, N: 14.03.
Calculated values: C: 38.73, H: 4.47, N: 14.56.

[Comparative Example 1] the Case of a Substance Containing No Sodium 0.30 g of the argIPQ disodium trihydrate obtained in Example 1 was mixed with 200 mL of water; and 1 g of concentrated hydrochloric acid was added thereto, stirred at room temperature for one night to thereby obtain a solution. The pH after the addition of the concentrated hydrochloric acid was 1.5. Thereafter, the solution was filtered, and washed with ethanol to thereby obtain a deposit. The obtained deposit was vacuum dried for 1 day to thereby obtain 0.23 g of an orange solid.

As a result of the measurements of the amount of sodium contained in the obtained solid and the amount of sodium contained in the argIPQ disodium trihydrate being a raw material by using a sodium (Na) electrode, the amount of sodium contained in the solid was 1/70 times the amount of sodium of the raw material.

(Solubility)

The argIPQ disodium trihydrate obtained in Example 1 (hereinafter, referred to also as "sample of Example 1") and the orange solid sample obtained in Comparative Example 1 (hereinafter, referred to also as "sample of Comparative Example 1") were each in about 20 mg mixed with 1 mL of water, and treated with ultrasonic waves for 5 min. The resultants were allowed to stand at the following temperatures (23° C. or 50° C.) for 1 hour, and thereafter centrifuged, and filtered with a filter of 0.5 μm; and the concentrations of the samples dissolved in water were determined by absorbances at an absorption wavelength of 260 nm. Their solubilities are shown below. There are also shown solubilities determined as in above except for altering 1 mL of water to 1 mL of ethanol and varying the temperatures (23° C. or 50° C.) to the following temperature (23° C.)

Sample of Example 1

23° C.: 37 g/L (water)
50° C.: 47 g/L (water)
23° C.: 0.4 g/L (ethanol)

Sample of Comparative Example 1

23° C.: 0.7 g/L (water)
50° C.: 1.1 g/L (water)
23° C.: 7.1 g/L (ethanol)

It was at least confirmed that the sample of Example 1 had a higher solubility in water than the sample of Comparative Example 1 containing no alkali metal. Further it was unexpectedly confirmed that the sample of Comparative Example 1 containing no alkali metal had a higher solubility in ethanol than the sample of Example 1.

(Cell Activity Test)

Human uterine cancer cells (HeLa cells) were cultured in an incubator at a 5%-$CO_2$ concentration and at 37° C. Thereafter, the human uterine cancer cells were inoculated to 96 wells so as to become 1000 cells/well, and cultured for one night. Then, a suspension in which the sample of Example 1 was suspended in a phosphate buffer so as to become 1 g/L was used and added so as to become 15.6 mg/mL. After 2 days, by using a "cell counting kit 8" (trade name, manufactured by Dojindo Laboratories), the number of the human uterine cancer cells was measured. When the number of the human uterine cancer cells 2 days after the culture for one night when the sample of Example 1 was not added was taken to be 100, the number of the cells when the sample of Example 1 in 15.6 mg/mL was used was 112.

With respect to the effect verified hitherto of promoting the cell proliferation, when the samples of the Examples are used as an ingredient of cosmetics, it can be expected that the samples proliferate cells of the skin and function as the effect of improving the condition of the skin. Further, when the samples of the Examples are used as a component of medicines or foods, it can be expected that the samples are administered to organisms (particularly humans), and in vivo function as the effect of improving the cell activity of damaged organs and improving organs whose function has lowered.

It was at least confirmed that the sample of Example 1 functioned to advance the cell proliferation.

INDUSTRIAL APPLICABILITY

The argIPQ salt according to the present invention is useful in the fields of medicines, cosmetics, foods (particularly, functional foods), feed and the like.

What is claimed is:

1. A compound of formula (1):

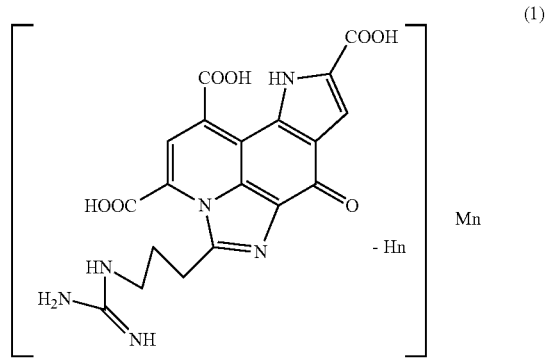

wherein
n is 1, 2, 3 or 4; and
M is an alkali metal or ammonium.

2. The compound according to claim 1,
wherein M is Na, K or Li.

3. The compound according to claim 2,
wherein the compound is a disodium salt.

4. The compound according to claim 3,
wherein the compound is a hydrous crystal.

5. A method for producing the compound of claim 3, the method comprising:
recovering a substance deposited from a reaction of a pyrroloquinoline quinone sodium salt with arginine to thereby obtain the compound.

6. The method of claim 5,
wherein in the recovering, an amount of the arginine to be used is 0.3 or more times and 5.0 or less times a mass of the pyrroloquinoline quinone sodium salt.

7. A medicine, comprising:
the compound of claim 1.

8. A cosmetic, comprising
the compound of claim 1.

9. A food, comprising
the compound of claim 1.

* * * * *